United States Patent
Sheppard et al.

(10) Patent No.: US 12,269,868 B2
(45) Date of Patent: Apr. 8, 2025

(54) ANTI-GALACTOFURANOSE ANTIBODIES FOR DETECTING AND TREATING ASPERGILLOSIS

(71) Applicants: THE ROYAL INSTITUTION FOR THE ADVANCEMENT OF LEARNING/MCGILL UNIVERSITY, Montréal (CA); THE GOVERNORS OF THE UNIVERSITY OF ALBERTA, Edmonton (CA)

(72) Inventors: Donald Christopher Sheppard, Westmount (CA); Benjamin Alfred William Rufus Ralph, Montréal (CA); Todd Lambert Lowary, Edmonton (CA); Susmita Sarkar, Edmonton (CA); Amira Ibrahim Aly Mohamed Khalil, Edmonton (CA)

(*) Notice: Subject to any disclaimer, the term of this patent is extended or adjusted under 35 U.S.C. 154(b) by 623 days.

(21) Appl. No.: 17/545,486

(22) Filed: Dec. 8, 2021

(65) Prior Publication Data

US 2022/0089701 A1   Mar. 24, 2022

Related U.S. Application Data

(62) Division of application No. 16/826,681, filed on Mar. 23, 2020, now Pat. No. 11,230,594.

(51) Int. Cl.
| | | |
|---|---|---|
| C07K 16/14 | (2006.01) | |
| A61K 38/00 | (2006.01) | |
| A61K 39/00 | (2006.01) | |
| C07K 14/725 | (2006.01) | |
| G01N 33/569 | (2006.01) | |

(52) U.S. Cl.
CPC .......... *C07K 16/14* (2013.01); *C07K 14/7051* (2013.01); *G01N 33/56961* (2013.01); *A61K 38/00* (2013.01); *A61K 2039/505* (2013.01); *C07K 2317/20* (2013.01); *C07K 2317/21* (2013.01); *C07K 2317/24* (2013.01); *C07K 2317/54* (2013.01); *C07K 2317/55* (2013.01); *C07K 2317/56* (2013.01); *C07K 2319/03* (2013.01); *G01N 2800/26* (2013.01)

(58) Field of Classification Search
CPC ...................................... C07K 16/14
See application file for complete search history.

(56) References Cited

U.S. PATENT DOCUMENTS

| 5,489,525 | A | 2/1996 | Pastan |
| 2015/0018532 | A1 | 1/2015 | Thorton |
| 2019/0178887 | A1 | 6/2019 | Herbst et al. |

FOREIGN PATENT DOCUMENTS

| WO | 2010082034 | 7/2010 |
| WO | 2014159764 | 10/2014 |

OTHER PUBLICATIONS

Lloyd et al., Protein Engineering, Design & Selection, 2009; 23(3):159-168 (Year: 2009).*
Campbell, A. Laboratory Techniques in Biochemistry and Molecular Biology, vol. 23, Chapter 1, 1991 (Year: 1991).*
Busby et al (bioRxiv preprint first posted online May 19, 2016; pp. 1-26 (Year: 2016).*

* cited by examiner

*Primary Examiner* — Brian Gangle
*Assistant Examiner* — Lakia J Jackson-Tongue
(74) *Attorney, Agent, or Firm* — NORTON ROSE FULBRIGHT CANADA LLP

(57) ABSTRACT

It is provided novel anti-galactofuranose antibodies and their use for diagnosis of and/or treating aspergillosis, and for the design of chimeric antigen receptor T-cells, wherein single chain variable fragment of the antibodies, such as a heavy chain variable region or a light chain variable region, is fused via a spacer and a transmembrane domain to a signaling endodomain to generate an expression cassette that will be integrated into a T cell.

11 Claims, 1 Drawing Sheet

Specification includes a Sequence Listing.

SEQUENCE LISTING

<160> NUMBER OF SEQ ID NOS: 8

<210> SEQ ID NO 1
<211> LENGTH: 1776
<212> TYPE: DNA
<213> ORGANISM: Artificial Sequence
<220> FEATURE:
<223> OTHER INFORMATION: BR1  heavy chain

<400> SEQUENCE: 1

| | | | | | |
|---|---|---|---|---|---|
| atggattttg | ggctgatttt | ttttattgtt | gctcttttaa | aaggggtcca | gtgtgaggtg | 60 |
| aagcttctcg | agtctggagg | tggcctggtg | cagcctggag | gatccctgaa | actctcctgt | 120 |
| gcagcctcag | gattcgattt | tagtagatac | tggatgagtt | gggtccggca | ggctccaggg | 180 |
| aaagggctag | aatggattgg | agaaattaat | ccagatagca | gtacgataaa | ctatacgcca | 240 |
| tctctaaagg | ataaattcat | catctccaga | gacaacgcca | aaaatacgct | gtacctgcaa | 300 |
| atgagcaaag | tgagatctga | ggacacagcc | ctttattact | gtgcaagacc | gagaggttac | 360 |
| tatgctatgg | actactgggg | tcaaggaacc | tcagtcaccg | tctcctcaga | gagtcagtcc | 420 |
| ttcccaaatg | tcttccccct | cgtctcctgc | gagagccccc | tgtctgataa | gaatctggtg | 480 |
| gccatgggct | gcctggcccg | ggacttcctg | cccagcacca | tttccttcac | ctggaactac | 540 |
| cagaacaaca | ctgaagtcat | ccagggtatc | agaaccttcc | caacactgag | gacaggggc | 600 |
| aagtacctag | ccacctcgca | ggtgttgctg | tctcccaaga | gcatccttga | aggttcagat | 660 |
| gaatacctgg | tatgcaaaat | ccactacgga | ggcaaaaaca | gagatctgca | tgtgcccatt | 720 |
| ccagctgtcg | cagagatgaa | ccccaatgta | aatgtgttcg | tcccaccacg | ggatggcttc | 780 |
| tctggccctg | caccacgcaa | gtctaaactc | atctgcgagg | ccacgaactt | cactccaaaa | 840 |
| ccgatcacag | tatcctggct | aaaggatggg | aagctcgtgg | aatctggctt | caccacagat | 900 |
| ccggtgacca | tcgagaacaa | aggatccaca | ccccaaacct | acaaggtcat | aagcacactt | 960 |
| accatctctg | aaatcgactg | gctgaacctg | aatgtgtaca | cctgccgtgt | ggatcacagg | 1020 |
| ggtctcacct | tcttgaagaa | cgtgtcctcc | acatgtgctg | ccagtccctc | cacagacatc | 1080 |
| ctaaccttca | ccatccccc | ctcctttgcc | gacatcttcc | tcagcaagtc | cgctaacctg | 1140 |
| acctgtctgg | tctcaaacct | ggcaacctat | gaaaccctga | atatctcctg | ggcttctcaa | 1200 |
| agtggtgaac | cactggaaac | caaaattaaa | atcatggaaa | gccatcccaa | tggcacctcc | 1260 |
| agtgctaagg | gtgtggctag | tgtttgtgtg | gaagactgga | ataacaggaa | ggaatttgtg | 1320 |
| tgtactgtga | ctcacaggga | tctgccttca | ccacagaaga | aattcatctc | aaaacccaat | 1380 |
| gaggtgcaca | acatccacc | tgctgtgtac | ctgctgccac | cagctcgtga | gcaactgaac | 1440 |
| ctgagggagt | cagccacagt | cacctgcctg | gtgaagggct | tctctcctgc | agacatcagt | 1500 |
| gtgcagtggc | ttcagagagg | gcaactcttg | ccccaagaga | agtatgtgac | cagtgccccg | 1560 |
| atgccagagc | ctggggcccc | aggcttctac | tttacccaca | gcatcctgac | tgtgacagag | 1620 |
| gaggaatgga | actccggaga | gacctatacc | tgtgttgtag | ccacgaggc | cctgccacac | 1680 |
| ctggtgaccg | agaggaccgt | ggacaagtcc | actggtaaac | ccacactgta | caatgtctcc | 1740 |
| ctgatcatgt | ctgacacagg | cggcacctgc | tattga | | | 1776 |

<210> SEQ ID NO 2
<211> LENGTH: 591
<212> TYPE: PRT
<213> ORGANISM: Artificial Sequence
<220> FEATURE:
<223> OTHER INFORMATION: BR1  heavy chain -continued

<400> SEQUENCE: 2

```
Met Asp Phe Gly Leu Ile Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
            35                  40                  45

Arg Tyr Trp Met Ser Trp Val Arg Gln Ala Pro Gly Lys Gly Leu Glu
50                  55                  60

Trp Ile Gly Glu Ile Asn Pro Asp Ser Ser Thr Ile Asn Tyr Thr Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Lys Val Arg Ser Glu Asp Thr Ala Leu Tyr
                100                 105                 110

Tyr Cys Ala Arg Pro Arg Gly Tyr Tyr Ala Met Asp Tyr Trp Gly Gln
            115                 120                 125

Gly Thr Ser Val Thr Val Ser Ser Glu Ser Gln Ser Phe Pro Asn Val
130                 135                 140

Phe Pro Leu Val Ser Cys Glu Ser Pro Leu Ser Asp Lys Asn Leu Val
145                 150                 155                 160

Ala Met Gly Cys Leu Ala Arg Asp Phe Leu Pro Ser Thr Ile Ser Phe
                165                 170                 175

Thr Trp Asn Tyr Gln Asn Asn Thr Glu Val Ile Gln Gly Ile Arg Thr
                180                 185                 190

Phe Pro Thr Leu Arg Thr Gly Gly Lys Tyr Leu Ala Thr Ser Gln Val
            195                 200                 205

Leu Leu Ser Pro Lys Ser Ile Leu Glu Gly Ser Asp Glu Tyr Leu Val
210                 215                 220

Cys Lys Ile His Tyr Gly Gly Lys Asn Arg Asp Leu His Val Pro Ile
225                 230                 235                 240

Pro Ala Val Ala Glu Met Asn Pro Asn Val Asn Val Phe Val Pro Pro
                245                 250                 255

Arg Asp Gly Phe Ser Gly Pro Ala Pro Arg Lys Ser Lys Leu Ile Cys
            260                 265                 270

Glu Ala Thr Asn Phe Thr Pro Lys Pro Ile Thr Val Ser Trp Leu Lys
            275                 280                 285

Asp Gly Lys Leu Val Glu Ser Gly Phe Thr Thr Asp Pro Val Thr Ile
290                 295                 300

Glu Asn Lys Gly Ser Thr Pro Gln Thr Tyr Lys Val Ile Ser Thr Leu
305                 310                 315                 320

Thr Ile Ser Glu Ile Asp Trp Leu Asn Leu Asn Val Tyr Thr Cys Arg
                325                 330                 335

Val Asp His Arg Gly Leu Thr Phe Leu Lys Asn Val Ser Ser Thr Cys
                340                 345                 350

Ala Ala Ser Pro Ser Thr Asp Ile Leu Thr Phe Thr Ile Pro Pro Ser
            355                 360                 365

Phe Ala Asp Ile Phe Leu Ser Lys Ser Ala Asn Leu Thr Cys Leu Val
            370                 375                 380

Ser Asn Leu Ala Thr Tyr Glu Thr Leu Asn Ile Ser Trp Ala Ser Gln
385                 390                 395                 400

Ser Gly Glu Pro Leu Glu Thr Lys Ile Lys Ile Met Glu Ser His Pro
```

```
                405                 410                 415
Asn Gly Thr Phe Ser Ala Lys Gly Val Ala Ser Val Cys Val Glu Asp
            420                 425                 430

Trp Asn Asn Arg Lys Glu Phe Val Cys Thr Val Thr His Arg Asp Leu
            435                 440                 445

Pro Ser Pro Gln Lys Lys Phe Ile Ser Lys Pro Asn Glu Val His Lys
            450                 455                 460

His Pro Pro Ala Val Tyr Leu Leu Pro Pro Ala Arg Glu Gln Leu Asn
465                 470                 475                 480

Leu Arg Glu Ser Ala Thr Val Thr Cys Leu Val Lys Gly Phe Ser Pro
                485                 490                 495

Ala Asp Ile Ser Val Gln Trp Leu Gln Arg Gly Gln Leu Leu Pro Gln
            500                 505                 510

Glu Lys Tyr Val Thr Ser Ala Pro Met Pro Glu Pro Gly Ala Pro Gly
            515                 520                 525

Phe Tyr Phe Thr His Ser Ile Leu Thr Val Thr Glu Glu Trp Asn
            530                 535                 540

Ser Gly Glu Thr Tyr Thr Cys Val Val Gly His Glu Ala Leu Pro His
545                 550                 555                 560

Leu Val Thr Glu Arg Thr Val Asp Lys Ser Thr Gly Lys Pro Thr Leu
                565                 570                 575

Tyr Asn Val Ser Leu Ile Met Ser Asp Thr Gly Gly Thr Cys Tyr
            580                 585                 590

<210> SEQ ID NO 3
<211> LENGTH: 705
<212> TYPE: DNA
<213> ORGANISM: Artificial Sequence
<220> FEATURE:
<223> OTHER INFORMATION: BR1 light chain

<400> SEQUENCE: 3
atggagtcac agattcaggt ctttgtattc gtgtttctct ggttgtctgg tgttgacgga        60
gacattgtga tgacccagtc tcacaaattc atgtccacat cagtaggaga cagggtcagc       120
atcacctgca aggccagtca ggatgtgagt actgctgtag cctggtatca acagaaacca       180
ggacaatctc ctaaactact gatttactcg gcatcctacc ggtacactgg agtccctgat       240
cgcttcactg gcagtggatc tgggacggat ttcactttca ccatcagcag tgtgcaggct       300
gaagacctgg cagtttatta ctgtcagcaa cattatagta ctccgtggac gttcggtgga       360
ggcaccaagc tggaaatcaa acgggctgat gctgcaccaa ctgtatccat cttcccacca       420
tccagtgagc agttaacatc tggaggtgcc tcagtcgtgt gcttcttgaa caacttctac       480
cccaaagaca tcaatgtcaa gtggaagatt gatggcagtg aacgacaaaa tggcgtcctg       540
aacagttgga ctgatcagga cagcaaagac agcacctaca gcatgagcag caccctcacg       600
ttgaccaagg acgagtatga acgacataac agctatacct gtgaggccac tcacaagaca       660
tcaacttcac ccattgtcaa gagcttcaac aggaatgagt gttag                       705

<210> SEQ ID NO 4
<211> LENGTH: 234
<212> TYPE: PRT
<213> ORGANISM: Artificial Sequence
<220> FEATURE:
<223> OTHER INFORMATION: BR1 light chain

<400> SEQUENCE: 4
```

```
Met Glu Ser Gln Ile Gln Val Phe Val Phe Val Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
            35                  40                  45

Val Ser Thr Ala Val Ala Trp Tyr Gln Gln Lys Pro Gly Gln Ser Pro
50                  55                  60

Lys Leu Leu Ile Tyr Ser Ala Ser Tyr Arg Tyr Thr Gly Val Pro Asp
65                  70                  75                  80

Arg Phe Thr Gly Ser Gly Ser Gly Thr Asp Phe Thr Phe Thr Ile Ser
            85                  90                  95

Ser Val Gln Ala Glu Asp Leu Ala Val Tyr Tyr Cys Gln Gln His Tyr
            100                 105                 110

Ser Thr Pro Trp Thr Phe Gly Gly Gly Thr Lys Leu Glu Ile Lys Arg
            115                 120                 125

Ala Asp Ala Ala Pro Thr Val Ser Ile Phe Pro Ser Ser Glu Gln
            130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
            165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
            195                 200                 205

His Asn Ser Tyr Thr Cys Glu Ala Thr His Lys Thr Ser Thr Ser Pro
            210                 215                 220

Ile Val Lys Ser Phe Asn Arg Asn Glu Cys
225                 230

<210> SEQ ID NO 5
<211> LENGTH: 1776
<212> TYPE: DNA
<213> ORGANISM: Artificial Sequence
<220> FEATURE:
<223> OTHER INFORMATION: BR2  heavy chain

<400> SEQUENCE: 5
atggattttg ggctgatttt ttttattgtt gctcttttaa aaggggtcca gtgtgaggtg      60
aagcttctcg agtctggagg tggcctggtg cagcctggag gatccctgaa actctcctgt    120
gaagcctcag gattcgattt tagtagatac tggatgaatt gggtccggca ggctccaggg    180
aaagggctag aatggattgg agaagttaat ccagatagca gtacgataaa ctatacgcct    240
tctctaaagg ataaattcat catctccaga gacaacgcca aaaatacgct gtatctgcaa    300
atgagtaaag tgtatctga ggacacagcc ctttatttct gtgcaagacc gagggggtaac    360 tacggtatag actactgggg tcaaggaacc tcagtcaccg tctcctcaga gagtcagtcc    420
ttcccaaatg tcttcccct cgtctcctgc gagagccccc tgtctgataa gaatctggtg    480
gccatgggct gcctggcccg ggacttcctg cccagcacca tttccttcac ctggaactac    540
cagaacaaca ctgaagtcat ccagggtatc agaaccttcc caacactgag gacagggggc    600
aagtacctag ccacctcgca ggtgttgctg tctcccaaga gcatccttga aggttcagat    660
gaatacctgg tatgcaaaat ccactacgga ggcaaaaaca gagatctgca tgtgcccatt    720
```

```
ccagctgtcg cagagatgaa ccccaatgta aatgtgttcg tcccaccacg ggatggcttc    780
tctggccctg caccacgcaa gtctaaactc atctgcgagg ccacgaactt cactccaaaa    840
ccgatcacag tatcctggct aaaggatggg aagctcgtgg aatctggctt caccacagat    900
ccggtgacca tcgagaacaa aggatccaca ccccaaacct acaaggtcat aagcacactt    960
accatctctg aaatcgactg gctgaacctg aatgtgtaca cctgccgtgt ggatcacagg   1020
ggtctcacct tcttgaagaa cgtgtcctcc acatgtgctg ccagtccctc acagacatc    1080 ctaaccttca ccatccccc ctcctttgcc gacatcttcc tcagcaagtc cgctaacctg    1140
acctgtctgg tctcaaacct ggcaacctat gaaaccctga atatctcctg ggcttctcaa    1200
agtggtgaac cactggaaac caaaattaaa atcatggaaa gtcatcccaa tggcaccttc    1260
agtgctaagg gtgtggctag tgtttgtgtg gaagactgga ataacaggaa ggaatttgtg    1320
tgtactgtga ctcacaggga tctgccttca ccacagaaga aattcatctc aaaacccaat    1380
gaggtgcaca acatccacc tgctgtgtac ctgctgccac cagctcgtga gcaactgaac    1440
ctgagggagt cagccacagt cacctgcctg gtgaagggct tctctcctgc agacatcagt    1500
gtgcagtggc ttcagagagg gcaactcttg ccccaagaga agtatgtgac cagtgccccg    1560
atgccagagc ctggggcccc aggcttctac tttacccaca gcatcctgac tgtgacagag    1620
gaggaatgga actccggaga gacctatacc tgtgttgtag ccacgaggc cctgccacac    1680 ctggtgaccg agaggaccgt ggacaagtcc actggtaaac ccacactgta caatgtctcc    1740
ctgatcatgt ctgacacagg cggcacctgc tattga                              1776
```

<210> SEQ ID NO 6
<211> LENGTH: 591
<212> TYPE: PRT
<213> ORGANISM: Artificial Sequence
<220> FEATURE:
<223> OTHER INFORMATION: BR2  heavy chain

<400> SEQUENCE: 6

```
Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Glu Ala Ser Gly Phe Asp Phe Ser
        35                  40                  45

Arg Tyr Trp Met Asn Trp Val Arg Gln Ala Pro Gly Lys Gly Leu Glu
    50                  55                  60

Trp Ile Gly Glu Val Asn Pro Asp Ser Ser Thr Ile Asn Tyr Thr Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Lys Val Ile Ser Glu Asp Thr Ala Leu Tyr
            100                 105                 110

Phe Cys Ala Arg Pro Arg Gly Asn Tyr Gly Ile Asp Tyr Trp Gly Gln
        115                 120                 125

Gly Thr Ser Val Thr Val Ser Ser Glu Ser Gln Ser Phe Pro Asn Val
    130                 135                 140

Phe Pro Leu Val Ser Cys Glu Ser Pro Leu Ser Asp Lys Asn Leu Val
145                 150                 155                 160

Ala Met Gly Cys Leu Ala Arg Asp Phe Leu Pro Ser Thr Ile Ser Phe
                165                 170                 175
```

```
Thr Trp Asn Tyr Gln Asn Asn Thr Glu Val Ile Gln Gly Ile Arg Thr
            180                 185                 190

Phe Pro Thr Leu Arg Thr Gly Gly Lys Tyr Leu Ala Thr Ser Gln Val
        195                 200                 205

Leu Leu Ser Pro Lys Ser Ile Leu Glu Gly Ser Asp Glu Tyr Leu Val
    210                 215                 220

Cys Lys Ile His Tyr Gly Gly Lys Asn Arg Asp Leu His Val Pro Ile
225                 230                 235                 240

Pro Ala Val Ala Glu Met Asn Pro Asn Val Asn Val Phe Val Pro Pro
                245                 250                 255

Arg Asp Gly Phe Ser Gly Pro Ala Pro Arg Lys Ser Lys Leu Ile Cys
            260                 265                 270

Glu Ala Thr Asn Phe Thr Pro Lys Pro Ile Thr Val Ser Trp Leu Lys
        275                 280                 285

Asp Gly Lys Leu Val Glu Ser Gly Phe Thr Thr Asp Pro Val Thr Ile
    290                 295                 300

Glu Asn Lys Gly Ser Thr Pro Gln Thr Tyr Lys Val Ile Ser Thr Leu
305                 310                 315                 320

Thr Ile Ser Glu Ile Asp Trp Leu Asn Leu Asn Val Tyr Thr Cys Arg
                325                 330                 335

Val Asp His Arg Gly Leu Thr Phe Leu Lys Asn Val Ser Ser Thr Cys
            340                 345                 350

Ala Ala Ser Pro Ser Thr Asp Ile Leu Thr Phe Thr Ile Pro Pro Ser
        355                 360                 365

Phe Ala Asp Ile Phe Leu Ser Lys Ser Ala Asn Leu Thr Cys Leu Val
    370                 375                 380

Ser Asn Leu Ala Thr Tyr Glu Thr Leu Asn Ile Ser Trp Ala Ser Gln
385                 390                 395                 400

Ser Gly Glu Pro Leu Glu Thr Lys Ile Lys Ile Met Glu Ser His Pro
                405                 410                 415

Asn Gly Thr Phe Ser Ala Lys Gly Val Ala Ser Val Cys Val Glu Asp
            420                 425                 430

Trp Asn Asn Arg Lys Glu Phe Val Cys Thr Val Thr His Arg Asp Leu
        435                 440                 445

Pro Ser Pro Gln Lys Lys Phe Ile Ser Lys Pro Asn Glu Val His Lys
    450                 455                 460

His Pro Pro Ala Val Tyr Leu Leu Pro Pro Ala Arg Glu Gln Leu Asn
465                 470                 475                 480

Leu Arg Glu Ser Ala Thr Val Thr Cys Leu Val Lys Gly Phe Ser Pro
                485                 490                 495

Ala Asp Ile Ser Val Gln Trp Leu Gln Arg Gly Gln Leu Leu Pro Gln
            500                 505                 510

Glu Lys Tyr Val Thr Ser Ala Pro Met Pro Glu Pro Gly Ala Pro Gly
        515                 520                 525

Phe Tyr Phe Thr His Ser Ile Leu Thr Val Thr Glu Glu Glu Trp Asn
    530                 535                 540

Ser Gly Glu Thr Tyr Thr Cys Val Val Gly His Glu Ala Leu Pro His
545                 550                 555                 560

Leu Val Thr Glu Arg Thr Val Asp Lys Ser Thr Gly Lys Pro Thr Leu
                565                 570                 575

Tyr Asn Val Ser Leu Ile Met Ser Asp Thr Gly Gly Thr Cys Tyr
            580                 585                 590
```

<210> SEQ ID NO 7
<211> LENGTH: 705
<212> TYPE: DNA
<213> ORGANISM: Artificial Sequence
<220> FEATURE:
<223> OTHER INFORMATION: BR2 light chain

<400> SEQUENCE: 7

```
atggagtcac agattcaggt ctttgtattc gtgtttctct ggttgtctgg cgttgacgga      60
gacattgtga tgacccagtc tcacaaattc atgtccacat cagtgggaga cagggtcagc     120
atcacctgca aggccagtca atatataatt acttctgttg cctggtatca acagaaacca     180
ggacaatctc ctaaaccact gatttactcg tcatcctacc ggtacactgg agtccctgat     240
cgcttcactg gcagtggatc tgggacggat ttcactttca ccatcatcag tgtgcaggct     300
gaagacctgg cagtttatta ctgtcaacaa cattttagta ttccgtggac gttcggtgga     360
ggcaccaagc tggaaatcaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga acgacataac agctatacct gtgaggccac tcacaagaca     660
tcaacttcac ccattgtcaa gagcttcaac aggaatgagt gttag                     705
```

<210> SEQ ID NO 8
<211> LENGTH: 234
<212> TYPE: PRT
<213> ORGANISM: Artificial Sequence
<220> FEATURE:
<223> OTHER INFORMATION: BR2 light chain

<400> SEQUENCE: 8

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Tyr
        35                  40                  45

Ile Ile Thr Ser Val Ala Trp Tyr Gln Gln Lys Pro Gly Gln Ser Pro
    50                  55                  60

Lys Pro Leu Ile Tyr Ser Ser Ser Tyr Arg Tyr Thr Gly Val Pro Asp
65                  70                  75                  80

Arg Phe Thr Gly Ser Gly Ser Gly Thr Asp Phe Thr Phe Thr Ile Ile
                85                  90                  95

Ser Val Gln Ala Glu Asp Leu Ala Val Tyr Tyr Cys Gln Gln His Phe
            100                 105                 110

Ser Ile Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

-continued

```
Tyr Ser Met Ser Ser Thr Leu Thr Leu Thr Lys Asp Glu Tyr Glu Arg
        195             200             205

His Asn Ser Tyr Thr Cys Glu Ala Thr His Lys Thr Ser Thr Ser Pro
    210             215             220

Ile Val Lys Ser Phe Asn Arg Asn Glu Cys
225             230
```

ANTI-GALACTOFURANOSE ANTIBODIES FOR DETECTING AND TREATING ASPERGILLOSIS

CROSS-REFERENCE TO RELATED APPLICATIONS

The present application is a divisional application of U.S. application Ser. No. 16/826,681 filed Mar. 23, 2020, the content of which is hereby incorporated by reference in its entirety.

TECHNICAL FIELD

It is provided novel anti-galactofuranose antibodies and their use for diagnostic and/or treating aspergillosis.

BACKGROUND

Members of the *Aspergillus* genus are opportunistic fungal pathogens that can cause the severe, often fatal disease, invasive aspergillosis (IA), in immunocompromised patients. *A. fumigatus* is the most common species to cause human disease, and can cause a number of severe pulmonary diseases. The current diagnostic test for aspergillosis is an antibody-based assay that has high rates of false positives, attributed to the lack of specificity and sensitivity of the antibody being used.

The mold *A. fumigatus* sheds immunogenic polysaccharides from its cell wall. This fungus secretes numerous polysaccharides that can elicit an immune response. In particular, the presence of the fungal polysaccharide, galactomannan, in bodily fluids is used as a marker of infection. An antibody raised against the galactofuranose portion of galactomannan is used in a diagnostic enzyme-linked immunosorbent assay (EIA) kit for the detection of fungal infections. This kit lacks both specificity and sensitivity, and routinely gives false positive results. As such, there is a need to develop more specific and sensitive antibodies compared to the one currently used.

It is thus highly desired to be provided with new antibodies against *Aspergillus fumigatus* and method of using same to diagnose and treat infections.

SUMMARY

It is provided an antibody, or a functional fragment thereof, comprising at least one of:
a) heavy chain encoded by the DNA sequence consisting of SEQ ID NO: 5;
b) a heavy chain amino acid sequence consisting of SEQ ID NO: 6;
c) a light chain encoded by the DNA sequence consisting of SEQ ID NO: 7;
d) a light chain amino acid sequence consisting of SEQ ID NO: 8;
e) a sequence with at least 85%, 90%, or alternatively 95% sequence identity to a), b) c) or d); and
f) a combination thereof.

It is also provided an antibody or a functional fragment thereof, comprising at least one of:
a) heavy chain encoded by the DNA sequence consisting of SEQ ID NO: 1;
b) a heavy chain amino acid sequence consisting of SEQ ID NO: 2;
c) a light chain encoded by the DNA sequence consisting of SEQ ID NO: 3;
d) a light chain amino acid sequence consisting of SEQ ID NO: 4; and
e) a combination thereof.

In another embodiment, the antibody comprises a heavy chain variable region encoded by the nucleotide sequence set forth in SEQ ID NO: 1.

In a further embodiment, the antibody comprises a heavy chain variable region consisting of SEQ ID NO: 2.

In an additional embodiment, the antibody comprises a light chain variable region encoded by the nucleotide sequence set forth in SEQ ID NO: 3.

In another embodiment, the antibody comprises a light chain variable region consisting of SEQ ID NO: 4.

In another embodiment, the antibody comprises a heavy chain variable region encoded by the nucleotide sequence set forth in SEQ ID NO: 5.

In a further embodiment, the antibody comprises a heavy chain variable region consisting of SEQ ID NO: 6.

In an additional embodiment, the antibody comprises a light chain variable region encoded by the nucleotide sequence set forth in SEQ ID NO: 7.

In another embodiment, the antibody comprises a light chain variable region consisting of SEQ ID NO: 8.

It is also encompassed herein are hybridoma cell lines producing the antibodies disclosed herein.

It is further provided a method of detecting aspergillosis in a patient comprising:
a) contacting the antibody as defined herein or a fragment thereof with a sample of said patient; and
b) detecting binding of the antibody to epitopes in the sample,
wherein binding of the antibody is indicative of the presence of an *Aspergillus* species in the sample.

In an embodiment, the binding of the antibody encompassed herein is detected by an immunoassay, such as e.g. a radioimmunoassay, a Western blot assay, an immunofluorescence assay, an enzyme immunoassay, an immunoprecipitation assay, a chemiluminescence assay, an electrochemiluminescence assay, an immunohistochemical assay, an immunoelectrophoresis assay, a dot blot assay, or a slot blot assay.

In a particular embodiment, the antibody provided herein is used as ELISA reagents. It is provided an ELISA kit comprising the antibody disclosed herein.

In an embodiment, the *Aspergillus* species is *Aspergillus fumigatus, Aspergillus flavus, Aspergillus niger, Aspergillus terreus*, or *Aspergillus nidulans*.

In an embodiment, it is provided a method of detecting a fungal infection in a patient comprising administering to the patient or a patient sample the antibody or a functional fragment thereof as described herein.

In an embodiment, the fungal infection is an aspergillosis infection.

In a further embodiment, the aspergillosis infection is caused by *Aspergillus fumigatus*.

In another embodiment, the patient sample is a urine sample.

In another embodiment, the method described herein further comprises administering an anti-galactofuranose antibody.

In an embodiment, the anti-galactofuranose antibody is EB-A2, AP3 or a combination thereof.

It is also provided a method of treating aspergillosis in a patient comprising administering the antibody defined herein or a fragment thereof to said patient.

In an embodiment, the method of treating aspergillosis as described herein comprises also administering an anti-galactofuranose antibody in combination with the antibody described herein.

In an embodiment, it is provided an expression cassette expressing a chimeric antigen receptor (CAR) comprising a heavy chain variable region and/or a light chain variable region as described herein.

In another embodiment, it is provided a vector comprising the expression cassette defined herein and a T cell which comprises the expression cassette as defined herein.

It is additionally provided a method for making a T cell which comprises the step of introducing an expression cassette as defined herein into a T cell.

It is further provided a pharmaceutical composition which comprises a T cell as defined herein together with a pharmaceutically acceptable carrier, diluent or excipient.

In an embodiment, the antibody is a humanized antibody, a monoclonal antibody or a polyclonal antibody.

In a further embodiment, the antibody is a mouse antibody, a goat antibody, a human antibody or a rabbit antibody.

In another embodiment, the antibody comprises an epitope binding fragment selected from the group consisting of: Fv, F(ab') and F(ab')$_2$.

In an additional embodiment, the antibody comprises a fluorochrome or a labeling molecule.

In an embodiment, the labeling molecule is biotin, peroxidase, alkaline phosphatase, glucoamylase, an oligonucleotide labeling, a radiolabel, a metal or β-galactosidase.

In an embodiment, the antibody or a functional fragment thereof encompassed herein comprises the heavy chain encoded by the DNA sequence consisting of SEQ ID NO: 1; the heavy chain amino acid sequence consisting of SEQ ID NO: 2; the light chain encoded by the DNA sequence consisting of SEQ ID NO: 3; and the light chain amino acid sequence consisting of SEQ ID NO: 4, and binds to a galactofuranose oligosaccharide.

In another embodiment, the antibody binds to a galactofuranose-containing oligosaccharide motif present in aspergillus galactomannan (GM).

In an embodiment, the antibody detects a polysaccharide comprising a mono-, di-, tri- and tetrasaccharides of galactofuranose.

In an embodiment, the galactofuranose oligosaccharide is:

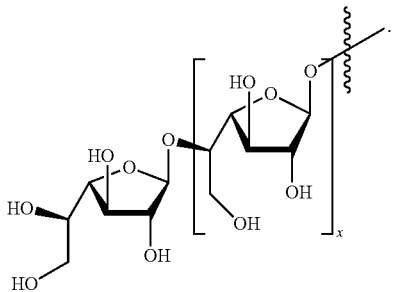

In an embodiment, X=0 to 20, preferably X=0 to 10, more preferably X=0 to 3.

the antibody is for detecting or treating aspergillosis.

In another embodiment, the antibody is attached to a solid support.

In an embodiment, the solid support is an immunostrip.

It is also provided a composition comprising the antibody or a functional fragment thereof as defined herein and a carrier.

In an embodiment, the composition comprises an expression cassette expressing a chimeric antigen receptor (CAR) and a single chain variable fragment of the antibody.

In another embodiment, the single chain variable fragment of the antibody is a heavy chain variable region or a light chain variable region.

In a further embodiment, the single chain variable fragment is fused via a spacer and a transmembrane domain to a signaling endodomain.

In an embodiment, the composition comprises a T cell, the T cell expressing the expression cassette.

In another embodiment, the composition comprises another anti-galactofuranose antibody.

In another embodiment, the fungal infection is measured by immunoassay.

In another embodiment, the immunoassay is a radioimmunoassay, a Western blot assay, an immunofluorescence assay, an enzyme immunoassay, an immunoprecipitation assay, a chemiluminescence assay, an electrochemiluminescence assay, an immunohistochemical assay, an immunoelectrophoresis assay, a dot blot assay, a slot blot assay, an ImmunoPET/MR or immunoPCR assay.

BRIEF DESCRIPTION OF THE DRAWINGS

Reference will now be made to the accompanying drawings.

DETAILED DESCRIPTION

Figure 1:
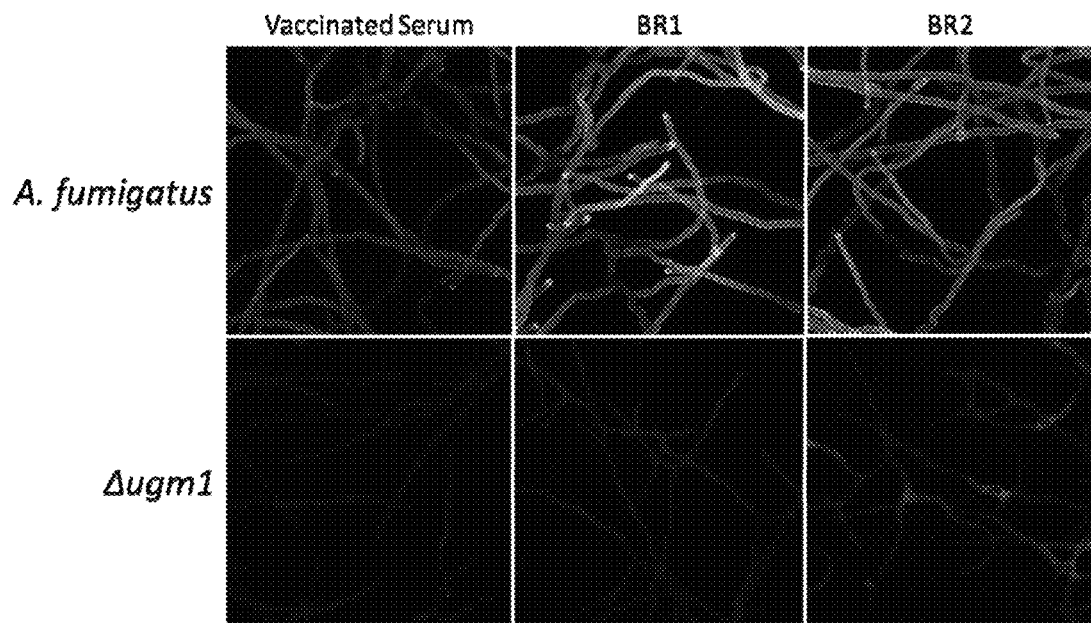
FIG. 1 illustrates IgM monoclonal antibodies from vaccinated mice recognizing *Aspergillus* GM. Binding of anti-Galf monoclonal antibodies or antibodies from vaccinated mice to wild-type and GM deficient (Δugm1) *A. fumigatus* as detected by indirect immunofluorescence with an Alexafluor 488 anti-mouse-IgM secondary and hyphae were counterstained with Draq5.

In accordance with the present description, there is provided novel anti-galactofuranose antibodies and their use for diagnostic and/or treating aspergillosis.

The mold *A. fumigatus* sheds immunogenic polysaccharides from its cell wall. In particular, the presence of the fungal polysaccharide, galactomannan, in bodily fluids is used as a marker of infection. Chimeric antigen receptor T-cell (CAR T-cell) technology has demonstrated that reprogrammed T-cells against fungal polysaccharides may prove to be an effective means to augment the host immune response during infection. Accordingly, it is proposed that antigen recognition sequences as provided herewith from anti-galactofuranose monoclonal antibodies can be used to construct chimeric T-cell antigen receptors that recognize galactofuranose within the fungal cell wall since these epitopes are absent from humans.

A glycoconjugate vaccine approach was used to immunize mice against neutropenic fungal infections. As a result of vaccination, the mice produced high antibody titers against the native polysaccharide which were further affinity matured after challenge with *A. fumigatus*. Splenocytes were isolated from vaccinated mice that survived the challenge, and monoclonal antibody producing hybridomas were generated. The minimal epitope for the antibodies produced by hybridomas producing BR1 and BR2 are a beta-(1-5)-linked galactofuranose disaccharide and a galactofuranose monosaccharide, respectively. Subsequent testing of these antibodies on various polysaccharide-deficient fungi demonstrated that these antibodies are highly specific for wild-type *Aspergillus*.

It is thus provided two antibodies, BR1 and BR2 which are IgM antibodies that can bind multiple antigen epitopes simultaneously. The provided antibodies bind shorter galactofuranose oligosaccharides than the existing monoclonal antibodies.

In an embodiment, it is provided an antibody identified as BR1 comprising the heavy chain encoded by the DNA sequence consisting of:

```
                                              (SEQ ID NO: 1)
ATGGATTTTGGGCTGATTTTTTTTATTGTTGCTCT

TTTAAAAGGGGTCCAGTGTGAGGTGAAGCTTCTCG

AGTCTGGAGGTGGCCTGGTGCAGCCTGGAGGATCC

CTGAAACTCTCCTGTGCAGCCTCAGGATTCGATTT

TAGTAGATACTGGATGAGTTGGGTCCGGCAGGCTC

CAGGGAAAGGGCTAGAATGGATTGGAGAAATTAAT

CCAGATAGCAGTACGATAAACTATACGCCATCTCT

AAAGGATAAATTCATCATCTCCAGAGACAACGCCA

AAAATACGCTGTACCTGCAAATGAGCAAAGTGAGA

TCTGAGGACACAGCCCTTTATTACTGTGCAAGACC

GAGAGGTTACTATGCTATGGACTACTGGGGTCAAG

GAACCTCAGTCACCGTCTCCTCAGAGAGTCAGTCC

TTCCCAAATGTCTTCCCCCTCGTCTCCTGCGAGAG

CCCCCTGTCTGATAAGAATCTGGTGGCCATGGGCT

GCCTGGCCCGGGACTTCCTGCCCAGCACCATTTCC

TTCACCTGGAACTACCAGAACAACACTGAAGTCAT

CCAGGGTATCAGAACCTTCCCAACACTGAGGACAG

GGGGCAAGTACCTAGCCACCTCGCAGGTGTTGCTG

TCTCCCAAGAGCATCCTTGAAGGTTCAGATGAATA

CCTGGTATGCAAAATCCACTACGGAGGCAAAAACA

GAGATCTGCATGTGCCCATTCCAGCTGTCGCAGAG

ATGAACCCCAATGTAAATGTGTTCGTCCCACCACG

GGATGGCTTCTCTGGCCCTGCACCACGCAAGTCTA

AACTCATCTGCGAGGCCACGAACTTCACTCCAAAA

CCGATCACAGTATCCTGGCTAAAGGATGGGAAGCT

CGTGGAATCTGGCTTCACCACAGATCCGGTGACCA

TCGAGAACAAAGGATCCACACCCCAAACCTACAAG

GTCATAAGCACACTTACCATCTCTGAAATCGACTG

GCTGAACCTGAATGTGTACACCTGCCGTGTGGATC

ACAGGGGTCTCACCTTCTTGAAGAACGTGTCCTCC

ACATGTGCTGCCAGTCCCTCCACAGACATCCTAAC

CTTCACCATCCCCCCCTCCTTTGCCGACATCTTCC

TCAGCAAGTCCGCTAACCTGACCTGTCTGGTCTCA

AACCTGGCAACCTATGAAACCCTGAATATCTCCTG

GGCTTCTCAAAGTGGTGAACCACTGGAAACCAAAA

TTAAAATCATGGAAAGCCATCCCAATGGCACCTTC

AGTGCTAAGGGTGTGGCTAGTGTTTGTGTGGAAGA

CTGGAATAACAGGAAGGAATTTGTGTGTACTGTGA

CTCACAGGGATCTGCCTTCACCACAGAAGAAATTC

ATCTCAAAACCCAATGAGGTGCACAAACATCCACC

TGCTGTGTACCTGCTGCCACCAGCTCGTGAGCAAC

TGAACCTGAGGGAGTCAGCCACAGTCACCTGCCTG

GTGAAGGGCTTCTCTCCTGCAGACATCAGTGTGCA

GTGGCTTCAGAGAGGGCAACTCTTGCCCCAAGAGA

AGTATGTGACCAGTGCCCCGATGCCAGAGCCTGGG

GCCCCAGGCTTCTACTTTACCCACAGCATCCTGAC

TGTGACAGAGGAGGAATGGAACTCCGGAGAGACCT

ATACCTGTGTTGTAGGCCACGAGGCCCTGCCACAC

CTGGTGACCGAGAGGACCGTGGACAAGTCCACTGG

TAAACCCACACTGTACAATGTCTCCCTGATCATGT

CTGACACAGGCGGCACCTGCTATTGA.
```

In an embodiment, said BR1 antibody comprises the following heavy chain amino acid sequence:

```
                                              (SEQ ID NO: 2)
MDFGLIFFIVALLKGVQCEVKLLESGGGLVQPGGS

LKLSCAASGFDFSRYWMSWVRQAPGKGLEWIGEIN

PDSSTINYTPSLKDKFIISRDNAKNTLYLQMSKVR

SEDTALYYCARPRGYYAMDYWGQGTSVTVSSESQS

FPNVFPLVSCESPLSDKNLVAMGCLARDFLPSTIS

FTWNYQNNTEVIQGIRTFPTLRTGGKYLATSQVLL

SPKSILEGSDEYLVCKIHYGGKNRDLHVPIPAVAE

MNPNVNVFVPPRDGFSGPAPRKSKLICEATNFTPK

PITVSWLKDGKLVESGFTTDPVTIENKGSTPQTYK

VISTLTISEIDWLNLNVYTCRVDHRGLTFLKNVSS

TCAASPSTDILTFTIPPSFADIFLSKSANLTCLVS

NLATYETLNISWASQSGEPLETKIKIMESHPNGTF

SAKGVASVCVEDWNNRKEFVCTVTHRDLPSPQKKF

ISKPNEVHKHPPAVYLLPPAREQLNLRESATVTCL

VKGFSPADISVQWLQRGQLLPQEKYVTSAPMPEPG

APGFYFTHSILTVTEEEWNSGETYTCVVGHEALPH

LVTERTVDKSTGKPTLYNVSLIMSDIGGTCY.
```

In an embodiment, it is provided an antibody identified as BR1 comprising the light chain encoded by the DNA sequence consisting of:

(SEQ ID NO: 3)
ATGGAGTCACAGATTCAGGTCTTTGTATTCGTGTT

TCTCTGGTTGTCTGGTGTTGACGGAGACATTGTGA

TGACCCAGTCTCACAAATTCATGTCCACATCAGTA

GGAGACAGGGTCAGCATCACCTGCAAGGCCAGTCA

GGATGTGAGTACTGCTGTAGCCTGGTATCAACAGA

AACCAGGACAATCTCCTAAACTACTGATTTACTCG

GCATCCTACCGGTACACTGGAGTCCCTGATCGCTT

CACTGGCAGTGGATCTGGGACGGATTTCACTTTCA

CCATCAGCAGTGTGCAGGCTGAAGACCTGGCAGTT

TATTACTGTCAGCAACATTATAGTACTCCGTGGAC

GTTCGGTGGAGGCACCAAGCTGGAAATCAAACGGG

CTGATGCTGCACCAACTGTATCCATCTTCCCACCA

TCCAGTGAGCAGTTAACATCTGGAGGTGCCTCAGT

CGTGTGCTTCTTGAACAACTTCTACCCCAAAGACA

TCAATGTCAAGTGGAAGATTGATGGCAGTGAACGA

CAAAATGGCGTCCTGAACAGTTGGACTGATCAGGA

CAGCAAAGACAGCACCTACAGCATGAGCAGCACCC

TCACGTTGACCAAGGACGAGTATGAACGACATAAC

AGCTATACCTGTGAGGCCACTCACAAGACATCAAC

TTCACCCATTGTCAAGAGCTTCAACAGGAATGAGT

GTTAG.

In an embodiment, said BR1 antibody comprises the following light chain amino acid sequence:

(SEQ ID NO: 4)
MESQIQVFVFVFLWLSGVDGDIVMTQSHKFMSTSV

GDRVSITCKASQDVSTAVAWYQQKPGQSPKLLIYS

ASYRYTGVPDRFTGSGSGTDFTFTISSVQAEDLAV

YYCQQHYSTPWTFGGGTKLEIKRADAAPTVSIFPP

SSEQLTSGGASVVCFLNNFYPKDINVKWKIDGSER

QNGVLNSWIDQDSKDSTYSMSSTLTLIKDEYERHN

SYTCEATHKTSTSPIVKSFNRNEC.

In an embodiment, it is provided an antibody identified as BR2 comprising the heavy chain encoded by the DNA sequence consisting of:

(SEQ ID NO: 5)
ATGGATTTTGGGCTGATTTTTTTTATTGTTGCTCT

TTTAAAAGGGGTCCAGTGTGAGGTGAAGCTTCTCG

AGTCTGGAGGTGGCCTGGTGCAGCCTGGAGGATCC

-continued

CTGAAACTCTCCTGTGAAGCCTCAGGATTCGATTT

TAGTAGATACTGGATGAATTGGGTCCGGCAGGCTC

CAGGGAAAGGGCTAGAATGGATTGGAGAAGTTAAT

CCAGATAGCAGTACGATAAACTATACGCCTTCTCT

AAAGGATAAATTCATCATCTCCAGAGACAACGCCA

AAAATACGCTGTATCTGCAAATGAGTAAAGTGATA

TCTGAGGACACAGCCCTTTATTTCTGTGCAAGACC

GAGGGGTAACTACGGTATAGACTACTGGGGTCAAG

GAACCTCAGTCACCGTCTCCTCAGAGAGTCAGTCC

TTCCCAAATGTCTTCCCCCTCGTCTCCTGCGAGAG

CCCCCTGTCTGATAAGAATCTGGTGGCCATGGGCT

GCCTGGCCCGGGACTTCCTGCCCAGCACCATTTCC

TTCACCTGGAACTACCAGAACAACACTGAAGTCAT

CCAGGGTATCAGAACCTTCCCAACACTGAGGACAG

GGGGCAAGTACCTAGCCACCTCGCAGGTGTTGCTG

TCTCCCAAGAGCATCCTTGAAGGTTCAGATGAATA

CCTGGTATGCAAAATCCACTACGGAGGCAAAAACA

GAGATCTGCATGTGCCCATTCCAGCTGTCGCAGAG

ATGAACCCCAATGTAAATGTGTTCGTCCCACCACG

GGATGGCTTCTCTGGCCCTGCACCACGCAAGTCTA

AACTCATCTGCGAGGCCACGAACTTCACTCCAAAA

CCGATCACAGTATCCTGGCTAAAGGATGGGAAGCT

CGTGGAATCTGGCTTCACCACAGATCCGGTGACCA

TCGAGAACAAAGGATCCACACCCCAAACCTACAAG

GTCATAAGCACACTTACCATCTCTGAAATCGACTG

GCTGAACCTGAATGTGTACACCTGCCGTGTGGATC

ACAGGGGTCTCACCTTCTTGAAGAACGTGTCCTCC

ACATGTGCTGCCAGTCCCTCCACAGACATCCTAAC

CTTCACCATCCCCCCCTCCTTTGCCGACATCTTCC

TCAGCAAGTCCGCTAACCTGACCTGTCTGGTCTCA

AACCTGGCAACCTATGAAACCCTGAATATCTCCTG

GGCTTCTCAAAGTGGTGAACCACTGGAAACCAAAA

TTAAAATCATGGAAAGTCATCCCAATGGCACCTTC

AGTGCTAAGGGTGTGGCTAGTGTTTGTGTGGAAGA

CTGGAATAACAGGAAGGAATTTGTGTGTACTGTGA

CTCACAGGGATCTGCCTTCACCACAGAAGAAATTC

ATCTCAAAACCCAATGAGGTGCACAAACATCCACC

TGCTGTGTACCTGCTGCCACCAGCTCGTGAGCAAC

TGAACCTGAGGGAGTCAGCCACAGTCACCTGCCTG

GTGAAGGGCTTCTCTCCTGCAGACATCAGTGTGCA

GTGGCTTCAGAGAGGGCAACTCTTGCCCCAAGAGA

```
AGTATGTGACCAGTGCCCCGATGCCAGAGCCTGGG

GCCCCAGGCTTCTACTTTACCCACAGCATCCTGAC

TGTGACAGAGGAGGAATGGAACTCCGGAGAGACCT

ATACCTGTGTTGTAGGCCACGAGGCCCTGCCACAC

CTGGTGACCGAGAGGACCGTGGACAAGTCCACTGG

TAAACCCACACTGTACAATGTCTCCCTGATCATGT

CTGACACAGGCGGCACCTGCTATTGA.
```

In an embodiment, said BR2 antibody comprises the following heavy chain amino acid sequence:

```
                                          (SEQ ID NO: 6)
MDFGLIFFIVALLKGVQCEVKLLESGGGLVQPGGS

LKLSCEASGFDFSRYWMNWVRQAPGKGLEWIGEVN

PDSSTINYTPSLKDKFIISRDNAKNTLYLQMSKVI

SEDTALYFCARPRGNYGIDYWGQGTSVTVSSESQS

FPNVFPLVSCESPLSDKNLVAMGCLARDFLPSTIS

FTWNYQNNTEVIQGIRTFPTLRTGGKYLATSQVLL

SPKSILEGSDEYLVCKIHYGGKNRDLHVPIPAVAE

MNPNVNVFVPPRDGFSGPAPRKSKLICEATNFTPK

PITVSWLKDGKLVESGFTTDPVTIENKGSTPQTYK

VISTLTISEIDWLNLNVYTCRVDHRGLTFLKNVSS

TCAASPSTDILTFTIPPSFADIFLSKSANLTCLVS

NLATYETLNISWASQSGEPLETKIKIMESHPNGTF

SAKGVASVCVEDWNNRKEFVCTVTHRDLPSPQKKF

ISKPNEVHKHPPAVYLLPPAREQLNLRESATVTCL

VKGFSPADISVQWLQRGQLLPQEKYVTSAPMPEPG

APGFYFTHSILTVTEEEWNSGETYTCVVGHEALPH

LVTERTVDKSTGKPTLYNVSLIMSDIGGTCY.
```

In an embodiment, it is provided an antibody identified as BR2 comprising the light chain encoded by the DNA sequence consisting of:

```
                                          (SEQ ID NO: 7)
ATGGAGTCACAGATTCAGGTCTTTGTATTCGTGTT

TCTCTGGTTGTCTGGCGTTGACGGAGACATTGTGA

TGACCCAGTCTCACAAATTCATGTCCACATCAGTG

GGAGACAGGGTCAGCATCACCTGCAAGGCCAGTCA

ATATATAATTACTTCTGTTGCCTGGTATCAACAGA

AACCAGGACAATCTCCTAAACCACTGATTTACTCG

TCATCCTACCGGTACACTGGAGTCCCTGATCGCTT

CACTGGCAGTGGATCTGGGACGGATTTCACTTTCA

CCATCATCAGTGTGCAGGCTGAAGACCTGGCAGTT

TATTACTGTCAACAACATTTTAGTATTCCGTGGAC
```

```
GTTCGGTGGAGGCACCAAGCTGGAAATCAAACGGG

CTGATGCTGCACCAACTGTATCCATCTTCCCACCA

TCCAGTGAGCAGTTAACATCTGGAGGTGCCTCAGT

CGTGTGCTTCTTGAACAACTTCTACCCCAAAGACA

TCAATGTCAAGTGGAAGATTGATGGCAGTGAACGA

CAAAATGGCGTCCTGAACAGTTGGACTGATCAGGA

CAGCAAAGACAGCACCTACAGCATGAGCAGCACCC

TCACGTTGACCAAGGACGAGTATGAACGACATAAC

AGCTATACCTGTGAGGCCACTCACAAGACATCAAC

TTCACCCATTGTCAAGAGCTTCAACAGGAATGAGT

GTTAG.
```

In an embodiment, said BR2 antibody comprises the following light chain amino acid sequence:

```
                                          (SEQ ID NO: 8)
MESQIQVFVFVFLWLSGVDGDIVMTQSHKFMSTSV

GDRVSITCKASQYIITSVAWYQQKPGQSPKPLIYS

SSYRYTGVPDRFTGSGSGTDFTFTIISVQAEDLAV

YYCQQHFSIPWTFGGGTKLEIKRADAAPTVSIFPP

SSEQLTSGGASVVCFLNNFYPKDINVKWKIDGSER

QNGVLNSWIDQDSKDSTYSMSSTLTLIKDEYERHN

SYTCEATHKTSTSPIVKSFNRNEC.
```

In an embodiment, the antibody encompassed herein is a humanized antibody, a monoclonal antibody or a polyclonal antibody.

Accordingly it is disclosed humanized antibodies and antibodies whose protein sequences can be modified to increase their similarity to antibody variants produced naturally in humans. Humanization can be necessary when the process of developing a specific antibody involves generation in a non-human immune system (such as that in mice). Antibody humanization methods are well known and designed to produce a molecule with minimal immunogenicity when applied to humans, while retaining the specificity and affinity of the parental non-human antibody. The protein sequences of antibodies produced in this way are partially distinct from homologous antibodies occurring naturally in humans, and are therefore potentially immunogenic when administered to human patients.

Humanized antibodies encompassed herein can be produced via enrichment technologies such as phage display or immunization of transgenic mice bearing the antibody human gene repertoire have provided powerful means to generate human antibodies.

In another embodiment, the antibody is a mouse antibody, a goat antibody, a human antibody or a rabbit antibody.

In an embodiment, the antibody comprises an epitope binding fragment selected from the group consisting of: Fv, F(ab') and F(ab')$_2$.

In another embodiment, the antibody comprises a heavy chain variable region encoded by the nucleotide sequence set forth in SEQ ID NO: 1.

In a further embodiment, the antibody comprises a heavy chain variable region consisting of SEQ ID NO: 2.

In an additional embodiment, the antibody comprises a light chain variable region encoded by the nucleotide sequence set forth in SEQ ID NO: 3.

In another embodiment, the antibody comprises a light chain variable region consisting of SEQ ID NO: 4.

In another embodiment, the antibody comprises a heavy chain variable region encoded by the nucleotide sequence set forth in SEQ ID NO: 5.

In a further embodiment, the antibody comprises a heavy chain variable region consisting of SEQ ID NO: 6.

In an additional embodiment, the antibody comprises a light chain variable region encoded by the nucleotide sequence set forth in SEQ ID NO: 7.

In another embodiment, the antibody comprises a light chain variable region consisting of SEQ ID NO: 8.

It is also provided a composition comprising the antibody as described herein and a carrier. The antibodies described herein may be employed in admixture with a suitable physiological or pharmaceutical carrier. Such compositions comprise a therapeutically effective amount of the antibody, and a physiologically or a pharmaceutically acceptable carrier or excipient. Such a carrier includes but is not limited to saline, buffered saline, dextrose, water, glycerol, ethanol, and combinations thereof. The formulation should suit the mode of administration.

An antibody as defined herein, can be administered alone or in combination with other antibodies directed toward other complementary targets.

In an embodiment, the antibodies provided herein can be used in a detection kit for aspergillosis.

In an embodiment, the antibodies provided herein further comprises a fluorochrome or a labeling, such as for example, biotin, peroxidase, an oligonucleotide labeling, a radiolabel, a metal, alkaline phosphatase, glucoamylase or β-galactosidase.

In another embodiment, the level of A. fumigatus are measured by immunoassay using the antibodies provided herein.

In an embodiment, the immunoassay is a radioimmunoassay, a Western blot assay, an immunofluorescence assay, an enzyme immunoassay, an immunoprecipitation assay, a chemiluminescence assay, an electrochemiluminescence assay, an immunohistochemical assay, an immunoelectrophoresis assay, a dot blot assay, a slot blot assay, an ImmunoPET/MR, or immunoPCR assay. The antibodies provided herein can be for example can be attached on a solid support.

In a particular embodiment, the antibodies provided herein are used as ELISA reagents. Encompassed herein is an ELISA kit comprising the antibodies disclosed herein.

The antibodies are collectively assembled in a kit with conventional immunoassay reagents for detection of A. fumigatus using an immunoassay. The kit may optionally contain both monoclonal and polyclonal antibodies and a standard for determining the presence of A. fumigatus in a sample. The kit containing these reagents provides for simple, rapid, on site detection. The antibodies described above are used as the basic reagents of a number of different immunoassays to determine the presence of A. fumigatus in a sample. The antibodies are employed in any type of immunoassay, whether qualitative or quantitative.

In another embodiment, the antibodies described herein further comprise a detectable label which is for example an enzyme. In more preferred embodiments, the enzyme is alkaline phosphatase, peroxidase, or β-galactosidase. In another embodiment, the enzyme produces a soluble reaction product.

In another embodiment, the enzyme produces a soluble or an insoluble reaction product. In another embodiment, the kit further comprises a substrate for the enzyme. Such immunoassays are also referred to enzyme-linked immunosorbent assays (ELISA).

The antibodies described above can also be employed in a lateral flow assay and/or an immunostrip. A solid phase format such as an immunostrip consist of test strips comprising multiple porous components, membranes and filters, through which liquid sample is drawn by capillary action.

One or more of the antibodies described above are employed in any heterogeneous or homogeneous, sandwich or competitive immunoassay for the detection of aspergillosis. Either the antibodies provided herein are labelled with a detectable label or coupled to a solid phase. Methods for coupling antibodies to solid phases are well known to those skilled in the art (e.g. direct coupling to a surface or also includes protein A/G catching of the antibody). In accordance with the immunoassay method, the sample containing A. fumigatus is reacted with the antibody for a sufficient amount of time under conditions that promote the binding of antibody to its antigen protein in the sample. A physical means is employed to separate reagents bound to the solid phase from unbound reagents such as filtration of particles, cell/particle sorting by FACS, decantation of reaction solutions from coated tubes or wells, magnetic separation, capillary action, and other means known to those skilled in the art. It will also be understood that a separate washing of the solid phase may be included in the method.

It is also encompassed herein are hybridoma cell lines producing the antibodies disclosed herein.

In an embodiment, it is encompassed the use of specific recognition sequences for the design of chimeric antigen receptor T-cells. Chimeric antigen receptors are known to be proteins which, in their usual format, combine the specificity of a monoclonal antibody (mAb) with the effector function of a T-cell. Their usual form is that of a type I transmembrane domain protein with an antigen recognizing amino terminus, a spacer, a transmembrane domain all connected to a compound endodomain which transmits T-cell survival and activation signals. For example, a common form of these molecules consist of fusions of single-chain variable fragments (scFv) derived from monoclonal antibodies such as the antibodies encompassed herein which recognize a target antigen, fused via a spacer and a transmembrane domain to a signaling endodomain. Such molecules result in activation of the T-cell in response to recognition by the scFv of its target. When T cells express such a CAR, they recognize and kill target cells that express the target antigen. It is thus encompassed CARs developed against A. fumigatus associated antigens using the antibody sequences and fragments provided herein.

In an embodiment, it is encompassed an expression cassette expressing a chimeric antigen receptor (CAR) comprising a heavy chain variable region and/or a light chain variable region as described herein. It is thus encompassed a vector comprising the expression cassette defined herein and a T cell which comprises the expression cassette as defined herein.

Also encompassed is a method for making a T cell or NK cell which comprises the step of introducing an expression cassette as defined herein into a T cell or NK cell. Also encompassed is a pharmaceutical composition which comprises a T cell as defined herein together with a pharmaceutically acceptable carrier, diluent or excipient.

It is further encompassed combining BR1 and/or BR2 with another anti-galactofuranose antibody. It is provided that such combination may exhibit increased sensitivity as compared to combination of known antibodies, including existing commercialized anti-galactofuranose antibody, such as for example but not limited to EB-A2 or AP3.

The present invention will be more readily understood by referring to the following examples which are given to illustrate the invention rather than to limit its scope.

EXAMPLE I

Isolation and Characterization of BR1 and BR2

Synthesis of TT-Galf$_4$

Tetanus toxoid (Statens Serum Institute) in PBS was added to propargyl linker to react overnight. Propargylated protein was then concentrated using a gel filtration column. BCA protein assay (Thermo Fisher) and MALDI-TOF MS were used to quantify the amount of protein and determine amino group modifications, respectively. Next, the propargylated protein was conjugated to Galf$_4$-N$_3$ by Azide-Alkyne Huisgen Cycloaddition as previously described. Briefly, the propargylated protein was incubated overnight in a sealed glass vial with the oligosaccharide in the presence of copper powder. After incubation, the reaction was quenched with EDTA and the protein washed with PBS. Finally, the conjugate was purified by gel filtration column. The resulting protein concentration and degree of oligosaccharide incorporation were assessed by BCA protein assay (Thermo Fisher) and MALDI-TOF MS respectively.

Immunizations

The day prior to immunization, TT-Galf$_4$ and alum (Alhydrogel®, Brenntag AG) were diluted to working concentrations and incubated on a rotary shaker overnight. Animals were immunized on day 0, 14, and 21 by administering a total of 6 µg TT-Galf$_4$ and 30 µg alum intraperitoneally, and 4 µg TT-Galf$_4$ and 20 µg alum subcutaneously. On day 31 serum was collected either from submandibular puncture (non-lethal) or cardiac puncture (lethal). Mice were infected on day 31 as detailed below.

Anti-Galf$_4$ ELISA and Monoclonal Antibody Epitope Mapping

High binding ELISA plates were coated overnight at 4° C. with 0.1 µg of bovine serum albumen (BSA)-Galf$_4$ (or other BSA glycoconjugates used for epitope mapping) in 100 µL PBS per well. Wells were washed with phosphate buffered saline+0.05% Tween™-20(PBS-T) and blocked with 1% BSA prepared in PBS. After washing, serially diluted serum samples or monoclonal antibodies in 0.1% BSA in PBS-T were added to the wells and incubated for 2 hours. Following washing, plates were incubated with 1:5000 diluted anti-mouse IgG or anti-mouse IgM secondary antibodies conjugated to horseradish peroxidase (Jackson ImmunoResearch Laboratories Inc.). After washing, the wells were developed with 200 µL tetramethylbenzidine (TMB) and the reaction was stopped with 100 µL 2N sulphuric acid. The absorbance was then read at 450 nm.

Immunofluorescence

Poly-D-lysine coverslips in 24-well plates were inoculated with 1×10$^5$ conidia in DMEM media and grown for 10 hours at 37° C. in 5% CO$_2$. Hyphae were gently washed three times between each step with PBS except where noted. Fungi were fixed with 4% PFA and blocked with a 50% fetal bovine serum, 1.5% BSA solution prepared in PBS. Serum samples were then diluted 1:500 in blocking solution and were added to unwashed coverslips for 1 hour at room temperature. Following washing, hyphae were incubated for an additional hour at room temperature in the dark in either anti-mouse or anti-rabbit IgG, A, M secondary antibodies conjugated to Alex Fluor® 488 (Invitrogen) that were diluted 1:500 in blocking buffer. Hyphae were then counterstained with DRAQ™ 5 (Invitrogen) diluted 1:1000 in PBS, washed and fixed in PFA. After a last set of washes, coverslips were mounted on slides and imaged using an LSM 780.

Infection Models

For systemic infection models, mice were infected with 3×10$^7$ conidia/mouse intravenously by tail vein injection on day 31 after initiation of immunization. For studies of pulmonary infection, mice were rendered neutropenic by treatment with 200 µg of anti-Ly6G (clone 1A8, BioxCell) antibodies intraperitoneally every 48 hours beginning the day prior to infection. On the day of infection, mice were anaesthetized by isoflurane then infected endotracheally with 1×10$^7$ conidia of *A. fumigatus* in a 50 µL volume of PBS containing 0.1% tween-80.

Generation of Monoclonal Antibodies

Monoclonal antibody producing hybridomas were generated from immunized mice surviving *A. fumigatus* challenge. Mice were immunized and challenged as described above. Fourteen days following infection, the spleens of mice that survived infection were harvested and transported fresh to MédiMabs (Montreal, Qc) for commercial immortalization of the splenocytes. Hybridomas were screened for the production of anti-Galf$_4$ antibodies by BSA-Galf$_4$ ELISA. The eleven stable hybridomas that were reactive by BSA-Galf$_4$ were then tested for their reactivity with native GM by immunofluorescence using hyphae of the wild-type (Af293) and Galf-deficient *A. fumigatus* (Δugm1).

Figure 2:
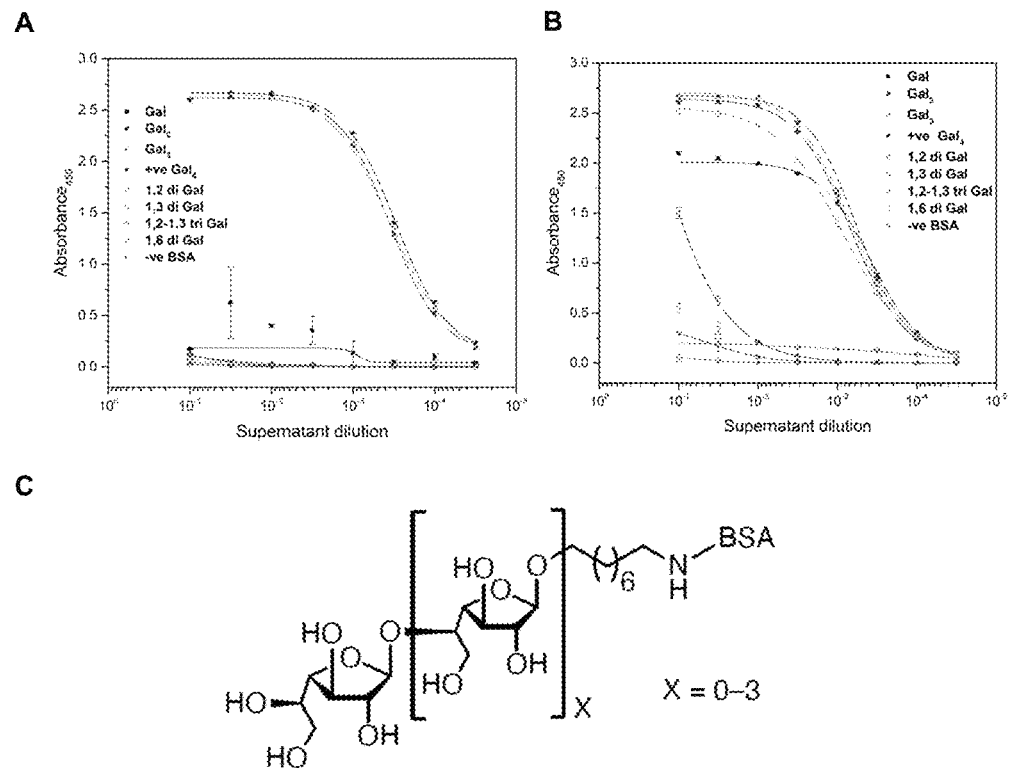
FIG. 2 illustrates the recognition of anti-Galf IgM monoclonal antibodies recognizing of galactofuranose oligosaccharides showing the specificity of BR1 (A) and BR2 (B) antibodies as measured by ELISA using the indicated panel of BSA-Galf glycoconjugates, and the structure of the minimum epitopes bound by BR1 and BR2 (C).

To determine if anti-Galf$_4$ antibodies could mediate protection against *A. fumigatus* challenge, monoclonal anti-Galf$_4$ antibodies were generated. Hybridomas were generated from splenocytes obtained from immunized mice that survived an *A. fumigatus* challenge. From a total of 600 hybridomas, 11 clones produced antibodies that bound to BSA-Galf$_4$ by ELISA. Of the 11 clones, two IgM antibody producing hybridomas (BR1 and BR2) were identified that produced antibodies specific against native GM polysaccharide as determined by immunofluorescence (FIG. 1). The antigen-specificity of the antibodies produced by these two clones was further assessed by testing antibody reactivity to a panel of glycoconjugates. Using this technique, the smallest recognizable epitope recognized by BR1 was determined to be a di-saccharide of β(1-5) linked Galf (se FIG. 2C) while BR2 was able to recognize Galf monosaccharide (FIG. 2D). To determine the ability of these antibodies to mediate protection against infection, naïve neutropenic mice were administered BR1 or BR2 antibodies beginning on the day of infection and 48 hours after. No difference in survival was observed between naïve mice, or those receiving either BR1 or BR2 antibody therapy.

While the present description has been described in connection with specific embodiments thereof, it will be understood that it is capable of further modifications and this application is intended to cover any variations, uses, or adaptations including such departures from the present disclosure as come within known or customary practice within the art and as may be applied to the essential features hereinbefore set forth, and as follows in the scope of the appended claims.

What is claimed is:

1. An antibody comprising:
a heavy chain amino acid sequence consisting of SEQ ID NO: 2;
and
a light chain amino acid sequence consisting of SEQ ID NO: 4.

2. The antibody of claim 1, wherein said antibody further comprises a fluorochrome or a labeling molecule.

3. The antibody of claim 2, wherein said labeling molecule is biotin, peroxidase, alkaline phosphatase, an oligonucleotide labeling, a radiolabel, a metal, glucoamylase or β-galactosidase.

4. The antibody of claim 1, wherein said antibody binds to a galactofuranose oligosaccharide.

5. The antibody of claim 4, wherein said antibody detects a polysaccharide comprising a mono-, di-, tri-, or tetrasaccharides of galactofuranose.

6. The antibody of claim 4, wherein said galactofuranose oligosaccharide is:

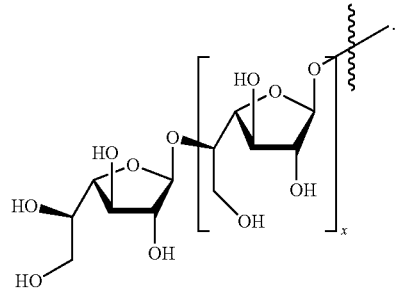

7. The antibody of claim 6, wherein X=0 to 20.

8. The antibody of claim 6, wherein X=0 to 10.

9. The antibody of claim 6, wherein X=0 to 3.

10. The antibody of claim 1, said antibody is attached to a solid support.

11. The antibody of claim 10, wherein the solid support is an immunostrip.

* * * * *